(12) United States Patent
Munro, III

(10) Patent No.: US 10,576,299 B1
(45) Date of Patent: Mar. 3, 2020

(54) RADIOACTIVE THERAPEUTIC DEVICE ABLE TO TURN SMALL RADII

(71) Applicant: John J Munro, III, North Andover, MA (US)

(72) Inventor: John J Munro, III, North Andover, MA (US)

( * ) Notice: Subject to any disclaimer, the term of this patent is extended or adjusted under 35 U.S.C. 154(b) by 199 days.

(21) Appl. No.: 15/600,905

(22) Filed: May 22, 2017

(51) Int. Cl.
*A61N 5/00* (2006.01)
*A61N 5/10* (2006.01)

(52) U.S. Cl.
CPC ......... *A61N 5/1017* (2013.01); *A61N 5/1007* (2013.01); *A61N 2005/1019* (2013.01); *A61N 2005/1094* (2013.01)

(58) Field of Classification Search
CPC .......... A61N 5/1007; A61N 2005/1008; A61N 2005/101
USPC .......................................................... 600/1–8
See application file for complete search history.

(56) References Cited

U.S. PATENT DOCUMENTS

| | | | | |
|---|---|---|---|---|
| 4,510,924 A | * | 4/1985 | Gray | A61N 5/1027 424/1.61 |
| 4,702,228 A | * | 10/1987 | Russell, Jr. | A61N 5/1027 600/8 |
| 4,754,745 A | * | 7/1988 | Horowitz | A61N 5/1007 600/8 |
| 4,861,520 A | | 8/1989 | van't Hooft et al. | |
| 5,154,705 A | | 10/1992 | Fleischhacker et al. | |
| 6,196,964 B1 | | 3/2001 | Loffler et al. | |
| 6,881,194 B2 | | 4/2005 | Miyata et al. | |
| 8,216,293 B2 | | 7/2012 | Ehrlinspiel et al. | |
| 8,444,544 B1 | | 5/2013 | Munro, III | |

FOREIGN PATENT DOCUMENTS

EP   0840572 B1   5/1998

OTHER PUBLICATIONS

Elekta, "Brachytherapy Applicator and Accessory Guide", www.elekta.com/brachytherapy; pp. 1 to 64, 2016. See pgs 6/14-6/15.
Elekta, "microSelectron Digital-Brachytherapy Afterloading Platform", www.elekta.com, pp. 5-2014, 1 pg.
Varian Medical Systems, "Varian Brachytherapy Applicators and Accessories", catalogue, 2011, pgs Ring and Tandem.
Varian Medical Systems, "GammaMedPlus iX, 3/24 iX Afterloaders—Feature Sheet", 2014, pp. 1 to 4, see 2 pgs.

* cited by examiner

*Primary Examiner* — John P Lacyk
(74) *Attorney, Agent, or Firm* — Stan Collier, Esq.

(57) ABSTRACT

The present invention provides a means for achieving greater ability to negotiate small radii like 5 mm of curvature in the human body to treat tumors, for example, with radioactive materials. This is accomplished by incorporating the source capsule into a flexible housing, which, in its simplest configuration, eliminates the direct connection of the source capsule to the driving cable, adding a degree of flexibility that is not available with a direct connection of the source capsule to the driving cable as in the presently available source capsules, and further providing segmented source capsules, and further providing devices for shielding of tissue using the segmented source assemblies.

12 Claims, 16 Drawing Sheets

X-Z Plane Dose Distribution
with Conical Collimator Opening
Focused 4 mm Below Center of Eye
(YRN4)

X-Z Plane Dose Distribution
with Conical Collimator Opening
Focused at Center of Eye
(YRZ0)

RADIOACTIVE THERAPEUTIC DEVICE ABLE TO TURN SMALL RADII

CROSS REFERENCES TO RELATED APPLICATIONS

NA

REFERENCE TO FEDERALLY SPONSORED RESEARCH OR DEVELOPMENT

NA

REFERENCE TO JOINT RESEARCH AGREEMENTS

NA

REFERENCE TO SEQUENCE LISTING

NA

BACKGROUND OF THE INVENTION

Field of the Invention

The present invention relates to the field of brachytherapy, and, in particular, treatment of tissues within the human body, and, in greater particularity, to devices able to navigate to locations requiring turning small radii to reach such tissues.

Description of the Prior Art

Ionizing radiation is employed in the management of a wide variety of malignant tumors, providing a mechanism whereby the malignancy can be destroyed while the normal tissues are preserved. With Preservation of normal tissues, normal function and normal appearance may also be preserved. Hence, ionizing radiation forms part of the treatment for over half of all patients with cancer.

The overall effectiveness of radiation therapy, however, depends upon the balance between effective tumor control and morbidity due to the treatment. It is understood that the differential effects of ionizing radiation on tumors and normal tissues gives rise to a favorable therapeutic ratio for most patients. However, radiation can have destructive immediately and with delayed effects on normal tissues. Techniques employed for radiation therapy significantly affect the incidence and severity of these destructive effects. The overall goal of radiation therapy is to maximize the effect of the radiation on tumor tissue while minimizing the effect of the radiation on normal tissue. Because the effect is generally proportional to the dose, this goal is generally accomplished by maximizing the dose to tumor tissue while minimizing the dose to normal tissue.

Various techniques have been developed to treat tumors in the body. In general, the use of radiation as a means to reduce or eliminate malignancy has been known for many years. One of the major issues in all of the techniques is the prevention of damage to healthy tissue.

Because all types of ionizing radiation affect tissues by means of the same basic physical mechanisms, differences in spatial or temporal distributions are responsible for different effects observed. The method for delivering radiation thus becomes highly significant.

The type of radiation treatment of malignant tumors most often performed involves directing a beam of radiation from a point external to the patient's body onto the area of the body in which the tumor is located, for the purpose of shrinking and ultimately destroying the tumor. This technique is known as "teletherapy" or external beam radiation therapy. Such treatment exposes normal healthy tissue to a high dose of radiation in the beam and consequently subjects the normal tissue to potential injury. Conventional external beam radiation treatments rely on multiple fractions of dose in order to ensure that the highest fractions of tumor cells are exposed at the most sensitive parts of the cell life cycle.

In contrast to external beam radiation therapy, brachytherapy is a method of radiation treatment of cancerous tissue in which the radiation source is placed in or near the cancerous tissue. Because of the proximity of the radiation source to the target tumor or cancerous tissue, brachytherapy treatment permits administration of a higher radiation dose to the tumor with better sparing of surrounding normal healthy tissues.

Because a delivered dose from a radiation source decreases proportionately to the square of the distance from that source, brachytherapy permits the delivery of very high radiation doses to those areas of a tumor in close proximity to the source, with relative sparing of more distant tissues. With careful placement, so that the radiation source is in proximity to the tumor or target tissue and distant from normal tissue, effective therapy against the tumor may be combined with minimal collateral damage to normal tissues.

Brachytherapy came into use as a treatment tool for cancer soon after the discovery of radium by Marie Curie in 1898. Goldberg and London used it for the treatment of facial basal cell carcinomas in 1903 with surface applicators.

Brachytherapy can be applied to cancer either by permanent implantation or by temporary application of removable sources. Permanent implantation results in the radioactive source, or sources, being left in the body in perpetuity, delivering their radiation dose until the radioactive material in the source has completely decayed away. Temporary application results in the radioactive source, or sources, being left only temporarily in or near the body, delivering their radiation only until the radioactive source or sources are removed.

A variety of radionuclides and methods for permanent or temporary implantation have been developed. A variety of radioisotopes, including $^{125}$Iodine, $^{103}$Palladium, $^{198}$Gold, $^{131}$Cesium, $^{137}$Cesium, $^{60}$Cobalt, $^{169}$Ytterbium and $^{192}$Iridium, have been used in the treatment of cancers involving such tissues as the breast, the prostate, the brain, lung, the head and neck, the female reproductive tract (including cervix, vagina, endometrium), rectum, esophagus, bronchus, bile duct, skin, pancreas, the musculoskeletal system and related soft tissue sarcomas, and the eye.

Temporary brachytherapy is a Process whereby the radioactive sources are placed into the body, usually using an applicator, such as a needle, catheter or other tubular apparatus, for a period of time to deliver the requisite radiation dose, and then the sources are removed. With this treatment modality, applicators are prepositioned in the patient. The sources are later temporarily placed within them. This procedure is known in the field as "afterloading."

Originally, temporary brachytherapy was performed using a technique that became known as "Low Dose Rate Brachytherapy." Using this technique, radioactive sources would be applied to provide a dose rate of 0.4 to 2 Gy/hour to the tumor. Using these techniques, treatment would take several days, during which period the patient would remain hospitalized. Low dose rate techniques utilized a variety of radioactive isotopes, including $^{125}$Iodine, $^{137}$Cesium, $^{198}$Gold and $^{192}$Iridium.

Later, a technique for "High Dose Rate Brachytherapy" was developed. In current practice, this high dose rate brachytherapy technique uses a source to provide dose rates in the range of or greater than 12 Gy/minute. This technique permitted the treatment to be performed in less than an hour, and without the hospitalization of the patient. These treatments are typically delivered in multiple fractions over several days or weeks.

This high dose rate brachytherapy method generally employs a highly radioactive source 14, FIG. 1, integrally attached to a driving cable 12, which together are known as a source assembly 10. An example of such a device may be found in the disclosure of van't Hooft in U.S. Pat. No. 4,861,520. A typical example is shown in FIG. 1 as prior art.

This source assembly 10 is typically delivered via a catheter or other applicator appliance through a natural cavity, duct or vessel of the body directly to the tumor site for localized irradiation. An alternative approach is to insert a closed-end needle directly into the tissue to be irradiated to create the channel for source delivery. This technique is less likely to expose normal healthy tissue to injury than if external beam radiation were used. One or more catheters, for example, may be implanted in the patient's body to provide a path from an external point to and through the tumor site, so that the interior of the tumor mass is accessible via the catheter(s). The radioactive source 10 is then mechanically delivered by pushing the source by means of the attached driving cable 12 through the catheter, not shown, for localized irradiation of the tumor for a very short period of time, usually in the range of only a few minutes per treatment.

The high dose rate source is securely located at the end of the source assembly, the other end of which is attached to a controllable apparatus known as a remote afterloader, for advancement or retraction. Advancement of the source assembly through the catheter to the proper locations for treatment of the tumor is achieved by pushing on the driving cable portion of the source assembly by an electro-mechanical device (afterloader). The source is left in the selected positions for predetermined time intervals (programmed into the afterloader) deemed necessary to provide the desired treatment, and is then automatically retracted and returned to a shielded storage area within the afterloader.

As described by van't Hooft in U.S. Pat. No. 4,861,520, the capsule 16 itself is quite long, i.e., 5.5 mm. This capsule 16 is welded to the driving cable 12, thereby effectively increasing the "effective length" by the length of the weld zone, which is ~1 mm. Therefore the effective solid length is ~6.5 mm. This effective solid length severely limits the flexibility of the source assembly and its ability to negotiate around curved channels in the body or in an applicator. This is particularly problematic when using a ring-type cervical applicator, such as those manufactured by Varian. These ring applicators have a minimum diameter of 26 mm (radius of curvature of 13 mm) which is limited by the ability of the source to negotiate the curved path. This problem was identified by Loffler et al. in U.S. Pat. No. 6,196,964. Loffler describes:

"a catheter normally has an inside diameter on the order of 1.5 mm or less. The length of a capsule depends on the desired strength of the radioactive source placed in the capsule, but should be on the order of several times the diameter, for instance in the range of 5 to 7 mm. The capsule itself and its connection with the guidewire are not flexible, so that the front part of the combination of guidewire and capsule has a relatively low degree of flexibility. Thus there is a certain probability that the capsule cannot pass the curves in a catheter with a strong curvature or only passes with difficulty.

For this purpose, FIG. 2, in the Prior art, a capsule 20 is attached to the guidewire, not shown, via an adapter 22, in which the adapter 22 comprises a cable or a thread with a flexibility greater than the flexibility of the guidewire. Thus, the solution was to incorporate an intermediate cable 24 of reduced diameter between the driving cable and the source capsule 20, FIG. 2, to increase the flexibility. Although this does provide a small degree of improvement, it still relies on a source capsule of ~5 mm length which in itself limits the flexibility. This is still insufficient to be able to negotiate all of the very small radius curvatures that may be encountered in high dose rate brachytherapy.

Another limitation, beyond flexibility, with the current brachytherapy sources is the limitation in the choice of radionuclide. In practice, the source capsules described by van't Hooft in U.S. Pat. No. 4,861,520 and Loftier et al. in U.S. Pat. No. 6,196,964 are used with $^{192}$Iridium, which produces relatively high energy photons, having principal photon emissions between 290 keV and 608 keV, and can be produced in relatively high specific activity. Also in this same geometrical configuration are sources of $^{60}$Cobalt, which can also be produced in relatively high specific activity and which produces even higher energy photons, having principal photon emissions between 1170 keV and 1330 key.

The radiation from a brachytherapy source is emitted nearly isotropically from the source, i.e., of equal intensity in all directions. This is disadvantageous in certain circumstances where the source may be located near to critical normal tissue, which needs to be spared from the radiation. It would be desirable to provide shielding around a portion of the radiation source to occlude, or absorb, the radiation being emitted in unwanted directions. However, the high photon energies associated with $^{192}$Iridium and $^{60}$Cobalt require thick amounts of dense material to achieve any significant reduction in the radiation dose. Therefore, it is very impracticable to provide shielding around these sources during a brachytherapy application or treatment.

The effectiveness of such shielding depends upon the energy of the emitted photons from the radiation source. Such shielding is more effective with lower energy radiation sources, lower in energy than $^{192}$Iridium. Examples of such sources include $^{169}$Ytterbium (principal photon energies between 50 keV and 308 keV), $^{181}$Tungsten (principal photon energies between 56 keV and 152 keV), $^{145}$Samarium (principal photon energies between 38 keV and 61 keV), $^{57}$Cobalt (principal photon energies between 122 keV and 136 keV), $^{153}$Gadolinium (principal photon energies between 41 keV and 103 keV), $^{170}$Thulium (principal photon energies between keV and 84 keV) et al. There are a variety of lower energy radionuclides that would be candidates for high dose rate brachytherapy. The photons from these radionuclides can be readily significantly shielded, with very thin amounts of shielding material, and therefore are more suitable to modulation. However, these radionuclides cannot be produced with sufficient specific activity to achieve a dose rate equivalent to that of the typical $^{192}$Iridium source within the same physical volume as the typical $^{192}$Iridium. Therefore, greater mass and greater volume of radioactive material is required to achieve the same radiation dose rate and treatment time as the standard $^{192}$Iridium source. And therefore, this larger volume requires a larger capsule than that described by van't Hooft in U.S. Pat. No. 4,861,520 and Loffler et al. in U.S. Pat. No. 6,196,964. This further exacerbates the issues relating to the ability to negotiate small radius curvatures in catheters and treatment applicators. For this reason, notwithstanding their desirability for dose modulation, these radionuclides have not been widely used for high dose rate brachytherapy.

Although there are devices for modulating radiation from a brachytherapy source (an example of such a device may be found in the disclosure of Munro in U.S. Pat. No. 8,444,544), the lack of flexibility in the source assembly has prevented widespread use in brachytherapy.

All articles, patents noted or cited, patent applications are incorporated by reference.

Accordingly, there is a need for a device having greater flexibility to reach locations within the body requiring traversing small radii.

SUMMARY OF THE INVENTION

The present invention provides a means for achieving greater ability to negotiate small radii of curvature. This is accomplished by incorporating the source capsule into a flexible housing, which, in its simplest configuration, eliminates the direct connection of the source capsule to the cable, adding a degree of flexibility that is not available with a direct connection of the source capsule to the driving cable as in the presently available source capsules. The invention is intended to reduce the outlined problem above and, in general, to make available a combination of a capsule and a guidewire that can be applied in a reliable way in a large number of situations, including situations in which strongly curved courses are to be passed in the catheter or the like.

Although it is possible that this flexible housing could be made of polymer, such a housing would not have the wear resistance, and therefore the durability, required for the repetitive delivery and retraction of the source during the lifetime of the source. (Elekta Nucletron notes the source is designed to withstand 25,000 cycles (https://www.elekta.com/dam/jcr:cbc09f98-d04e-4262-a082-37d7d189577a/MicroSelectron %20brochure.pdf)(See Reliable) Varian notes their source is designed to withstand 5,000 cycles https://www.varian.com/sites/default/files/resource attachments/GammaMedplus %20iX %20FeatureSheet_RAD4249.pdf)(See Gamma MedPlus pg.). Furthermore, the standards applicable to these sources (International Standard 2919; American National Standard N432) and the regulations that invoke these standards require the source assembly to withstand a temperature of 600° C., which is beyond the useful range of polymers. Therefore, the flexible housing of this invention is, by necessity of the application, made from metal.

It is an object of the present invention to provide a device for use in brachytherapy;

It is another object of the present invention to provide a device having the source capsule in a flexible housing;

It is a further object of the present invention to provide a device where the source capsule is not directly connected to the driving cable;

It is still a further object of the present invention to provide a device having a flexible housing and being made of metal;

It is still another object of the present invention to provide flexible housing having small radii of curvatures, and having applicators for the flexible housing specifically design for human organs.

These and other objects, features, and advantages of the present invention will become more readily apparent from the attached drawings and the detailed description of the preferred embodiments, which follow.

DETAILED DESCRIPTION OF THE PREFERRED EMBODIMENTS

Figure 1:
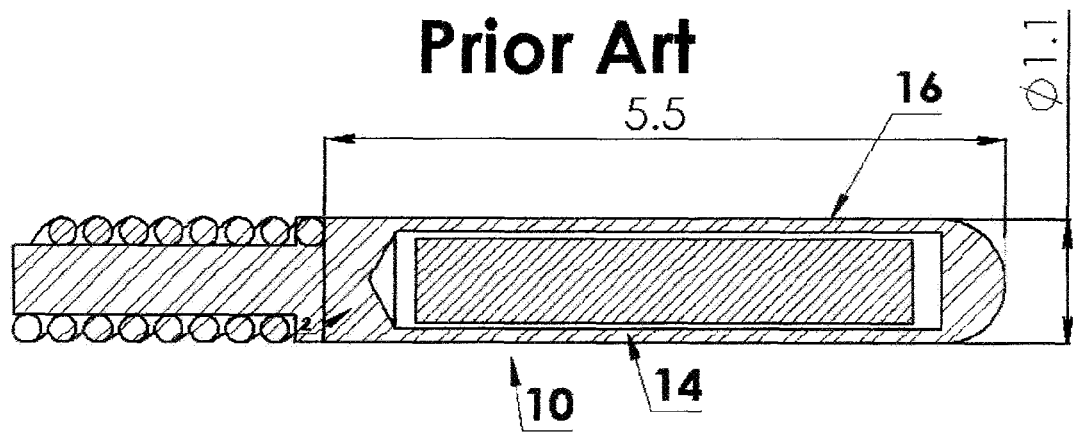
FIG. 1 shows in cross section a radioactive source integrally attached to a driving cable known as a source assembly and is prior art.
Figure 2:
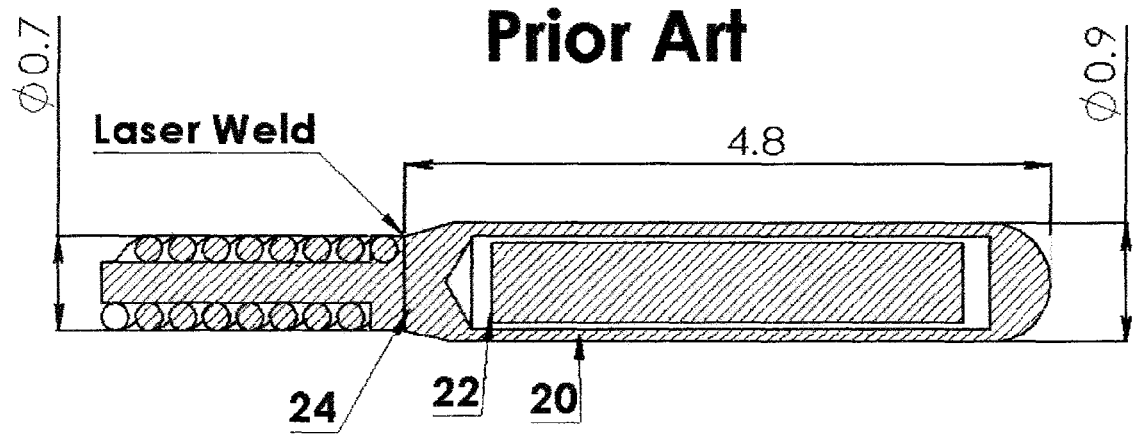
FIG. 2 shows in cross section a radioactive source integrally attached to a reduced diameter driving cable known as a source assembly and is prior art.
Figure 3:
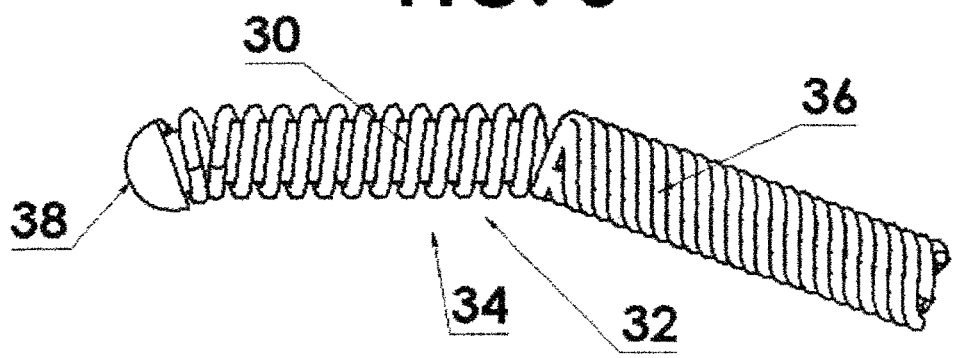
FIG. 3 shows a flexible housing in the form of a helically wound wire with a single source capsule residing within the spring and attached to the driving cable thereby increasing the flexibility thereof.
Figure 4:
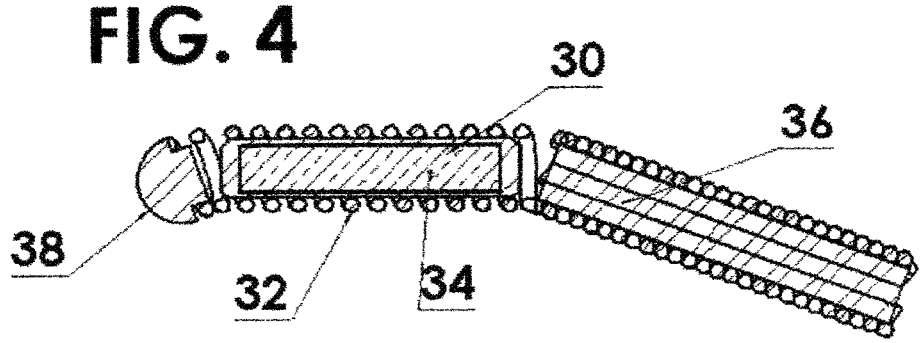
FIG. 4 is a cross section view of FIG. 3.
Figure 24:
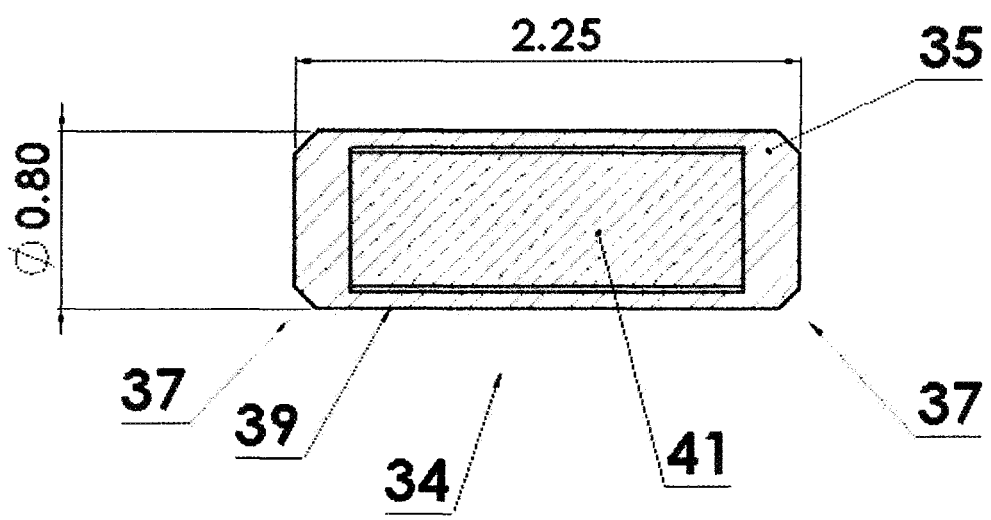
FIG. 24 is a cross section view through a single source capsule showing the nuclear material therein.

In one embodiment of the present invention, referring to FIGS. 3 and 4, a flexible housing 30 is in the form of a helically wound wire 32 such as a coil/spring. The source capsule 34 resides within the helically wound wire 32 as shown in FIGS. 3 and 4. The helically wound wire 32 is attached to a driving cable 36. However, since the source capsule 34 itself is not attached to the driving cable 36 nor to the "nose piece" 38 nor to the flexible housing 30, the helically wound wire 32 is free to bend along the curvature both distal to and proximal to the source capsule 34, resulting in a shorter effective length than if the source capsule 34 were attached directly to the driving cable 36. Referring to FIG. 24, a cross sectional view of one source capsule 34 is shown. The source capsule 34 has a cylindrical housing 35 with truncated ends 37 and an interior cylindrical volume 39 with a cylindrical nuclear material 41 or pellet 40 therein as will be described below in greater detail. The cylindrical ends 37 are welded onto the housing 35. The truncated ends 37 aid in flexing when more than one capsule is inserted into the flexible housing 30. In general the capsule as shown herein may range in diameter from about 0.5 to about 1.5 mm and have a length from about 2 to 10 mm.

Figure 5:
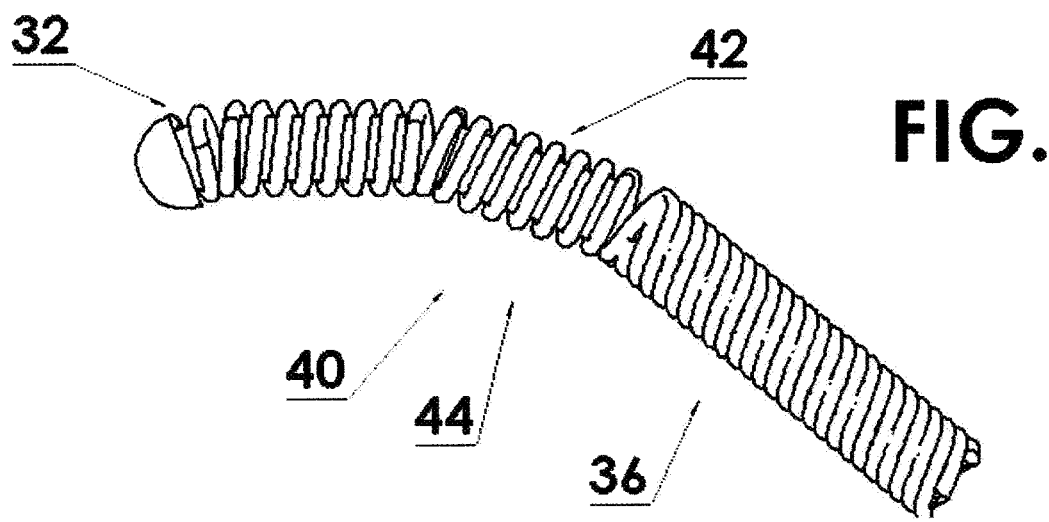
FIG. 5 shows a flexible housing in the form of a helically wound wire with two source capsules residing within the spring and attached to the driving cable thereby increasing the flexibility thereof.
Figure 6:
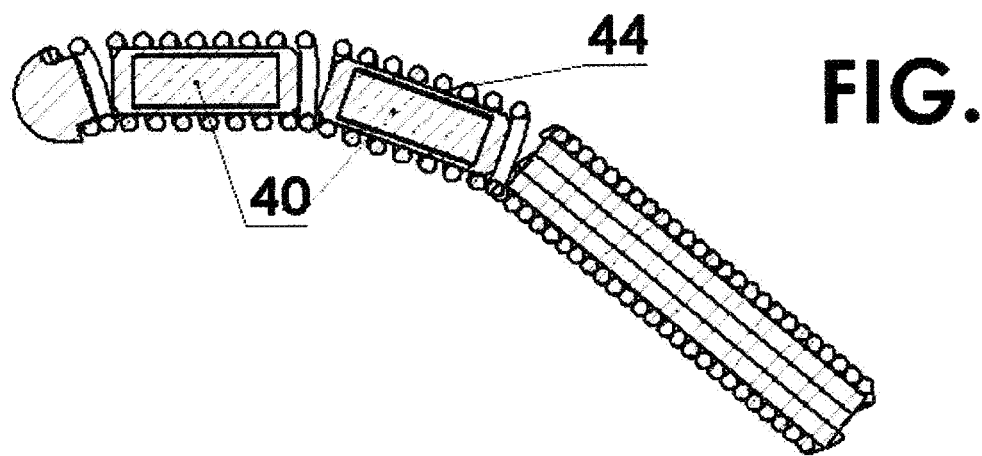
FIG. 6 is a cross sectional view of FIG. 5.

In another embodiment, referring to FIGS. 5 and 6, the radioactive element material can be in the form of two, or more, pellets 40 or source capsules 40, each with a fraction (half, or some other fraction) of the radioactivity of the radioactive element material in the above embodiment where there is only one capsule 34. In this case, in addition to the improved flexibility distal to and proximal to the radioactive source(s), the helically wound wire 32 is free to bend at point 42 between the pair of source capsules 40. This is shown, for a source assembly 44 of two source capsules, in FIGS. 5 and 6. However, it is clear that this could include a greater number of segmented individual source capsules and thereby increase the flexibility further as will be shown below.

Figure 7:
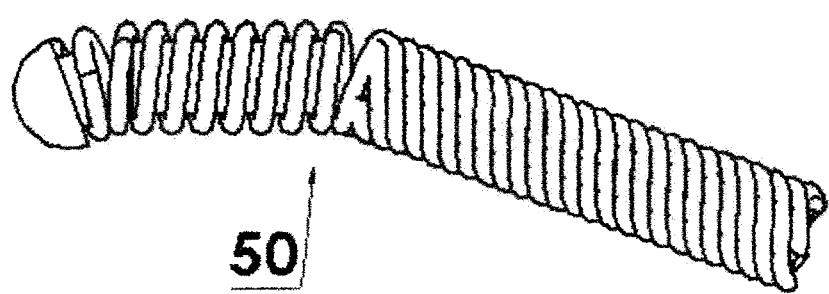
FIG. 7 shows a flexible housing in the form of a helically wound wire with a single source capsule residing (the radioactivity being produced from isotopically enriched target material) within the spring and attached to the driving cable thereby increasing the flexibility thereof due to the small size of the capsule needed.
Figure 8:
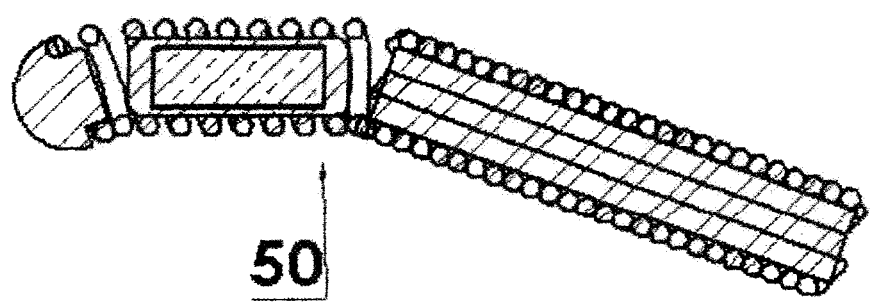
FIG. 8 is a cross section view of FIG. 7.

In another embodiment, the radioactive element material can be made using isotopically enriched target material. In the case of Iridium, which naturally contains 37.4% $^{191}$Iridium, an enrichment of 80% or more could be used. In this case, the specific activity would be increased by a factor of ~2, resulting in an active element of only half the size as that in the standard source capsule 50. Therefore, in this case, the flexibility is increased even further, as shown in FIGS. 7 and 8 due to the smaller length of the capsule 50.

Figure 9:
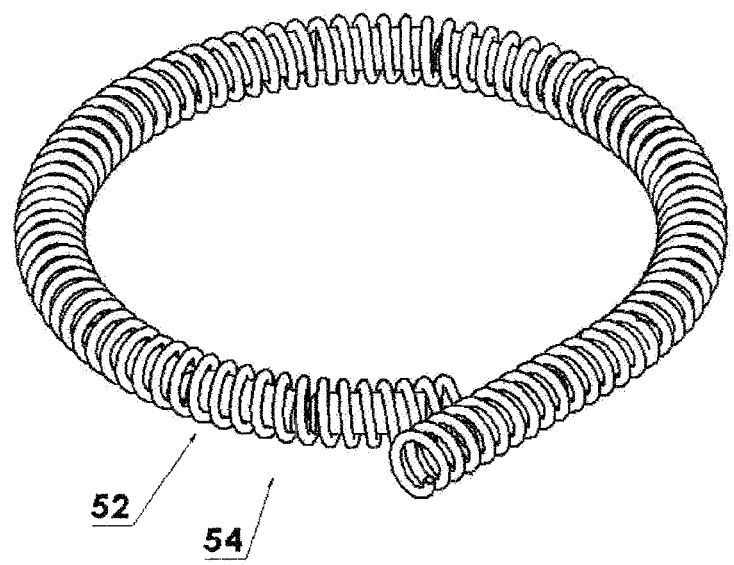
FIG. 9 shows a flexible housing in the form of a helically wound wire with a multitude or segmented source capsules residing within the spring and attached to the driving cable thereby increasing the flexibility thereof.
Figure 10:
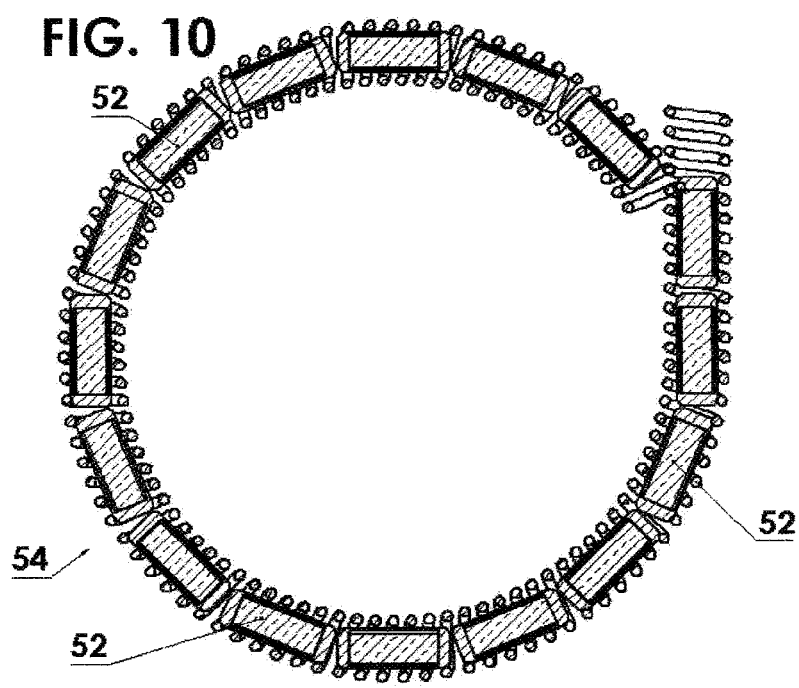
FIG. 10 is a cross sectional view of FIG. 9.

In another embodiment as shown in FIGS. 9 and 10, which is particularly useful in cases where the activity and/or the specific activity is sufficiently low that treatment/exposure times are long, (such as is the case when using the lower energy radionuclides described above) multiple source capsules 52 can be employed in a single source assembly 54 while maintaining the flexibility to negotiate very small bend radii. An example of this is shown in FIGS. 9 and 10.

Figure 11:
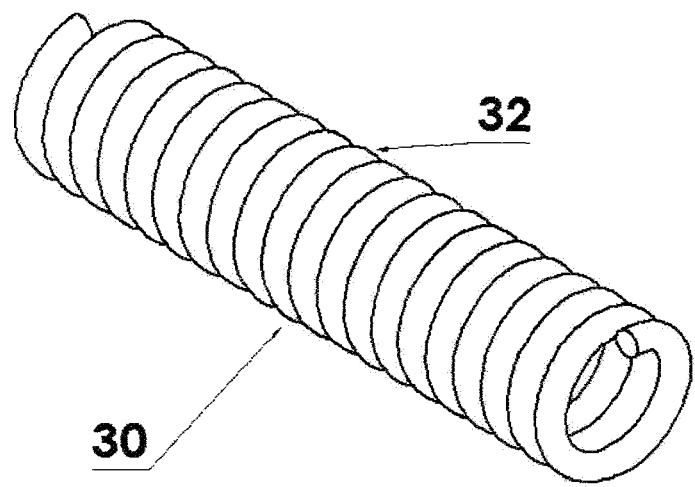
FIG. 11 shows a flexible housing for the source being fabricated using a helical coil with a round cross section.
Figure 12:
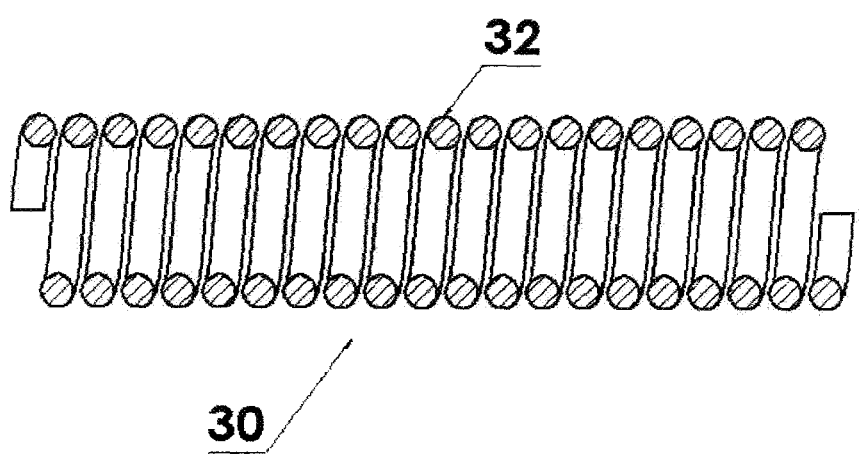
FIG. 12 is a cross sectional view of FIG. 11.
Figure 13:
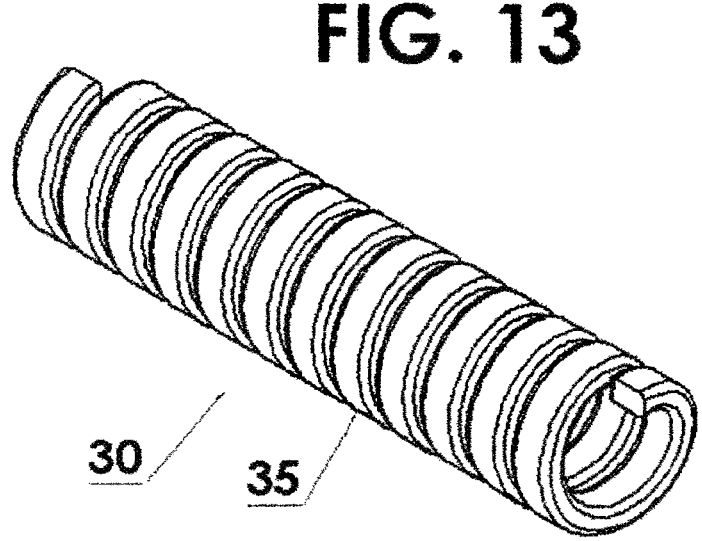
FIG. 13 is a flexible housing for the source being fabricated using a helical coil with a rectangular cross section.
Figure 14:
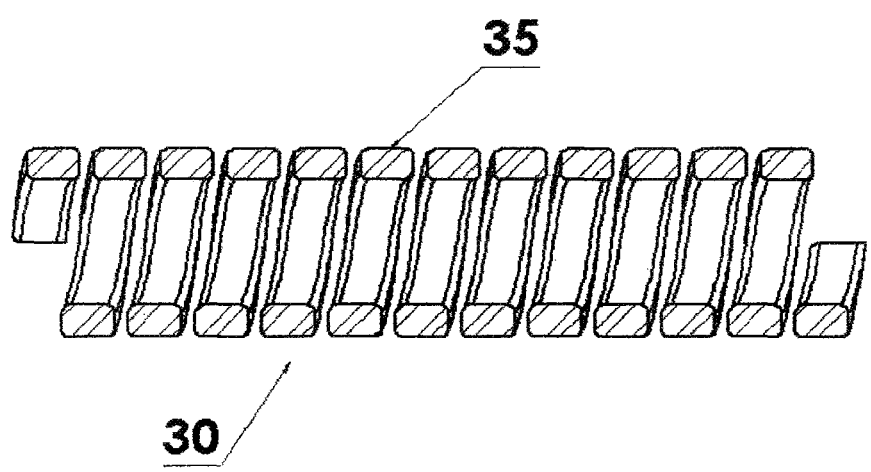
FIG. 14 is a cross sectional view of FIG. 13.

The above examples describe the flexible housing 30 for the source being fabricated using a helical coil using wire 32 with a round cross section 33 as seen in FIGS. 11 and 12. However, this invention is not limited to round cross sections. Other forms, such as rectangular cross sections 35 and other geometric shapes, are possible. See FIGS. 13 and 14.

Figure 25:
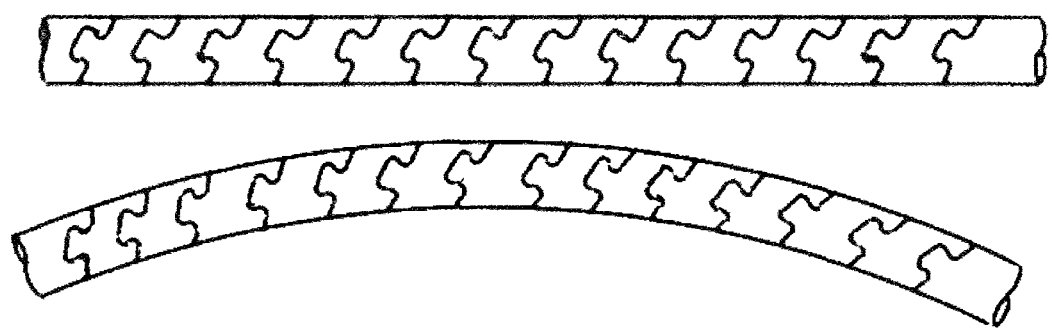
FIG. 25 is a view of a flexible housing made for the Present invention using laser cutting of tube.

Moreover, this invention is not limited to helically wound coils. Other forms of flexible tubular elements that can contain the radioactive source elements and maintain flexibility as claimed are also possible. One embodiment is a helical convolute pattern laser cut into a cannulated bar that transforms the material from an inflexible solid tube into an engineered flexible shaft. The helical convolute pattern has interlocking features to improve bending and axial strength. Varying degrees of flexibility through various laser cut patterns is possible. Examples of such patterns are described in European Patent EP 0840572 B2 and U.S. Pat. No. 6,053,922 to Krause, et al. and one is shown in FIG. 25. Another example is a flexible shaft as described in U.S. Pat. No. 8,216,293 to Ehrlinspiel, et al. which consists of a plurality of adjacently abutting cells, he walls of which are formed from wall sections of the tube (See FIG. 6 of this patent). Another embodiment is a wire-stranded hollowtube as described in U.S. Pat. No. 6,881,194 to Miyata, et al. This embodiment can consist of a single layer of wire strand or multiple layers of wire stands. Another example is a hollow lumen cable as described in U.S. Pat. No. 5,154,705 to Fleischhackert, et al. The possibilities are greatly increased by use of 3D printing. Each of these embodiments includes a flexible outer tubular element to which is incorporated one or more radioactive source capsules to create this present invention.

Figure 15:
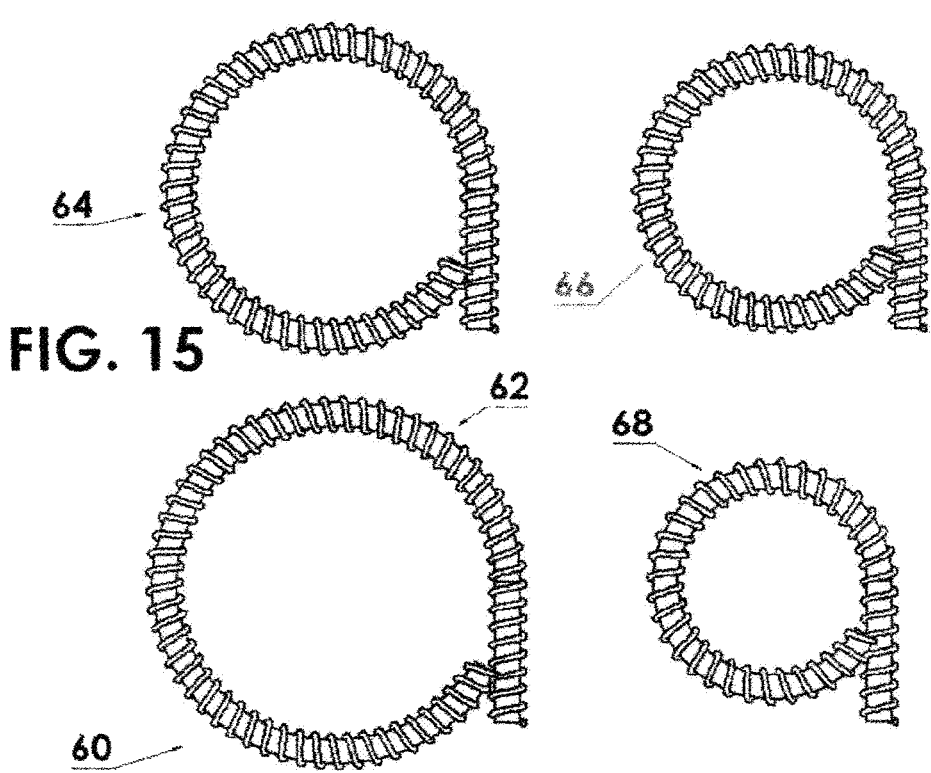
FIG. 15 shows four ring source assemblies having diameters from 1.6 (upper left), 14 m (lower left), 12 mm (upper right) and 10 mm (lower right)

This increased flexibility has very important implications in the field of high dose rate brachytherapy. As noted above, the current ring applicators used in the treatment of cervical cancer are limited to a diameter of 26 mm due to the inflexibility of the traditional high dose rate brachytherapy source. As shown in FIG. 15, employing source capsules of this invention allows the rings 60, four shown, of diameters of 16 mm (lower left) 62, 14 mm (upper left) 64, 12 mm (upper right) 66, and even as small as 10 mm (lower right) 68.

In addition to the application noted above relating to gynecological cervix brachytherapy, the ability of the source assembly to negotiate very small bend radii has a particular benefit in other applications where negotiation/maneuvering around small bend radii are necessary to effect the treatment, such as in treatment of the eye, or the biliary duct. Also, for treatment of the skin, the ability to negotiate small bend radii allows the treatment to be more conformal (to the tumor/target) than the current conventional treatments that are limited by the flexibility of the source assembly.

This invention, with the ability of creating an array of sources of lower activity such that the total activity results in a dose rate equivalent to that of the typical $^{192}$Iridium source while maintaining the flexibility required to navigate small radius curvatures in body channels with an applicator has very important implications in the field of high dose rate brachytherapy. As noted above, this permits the use of lower-energy radionuclides without loss of flexibility, and therefore facilitates the use of partial shielding of the applicator in curved geometries, resulting in better conformality (of the dose to the target), and therefore better achieving the goal of maximizing the effect of the radiation on tumor tissue while minimizing the effect of the radiation on normal tissue by maximizing the dose to tumor tissue while minimizing the dose to normal tissue. The ability to partially shield these sources in curved geometry has very important applications in brachytherapy.

Figure 16:
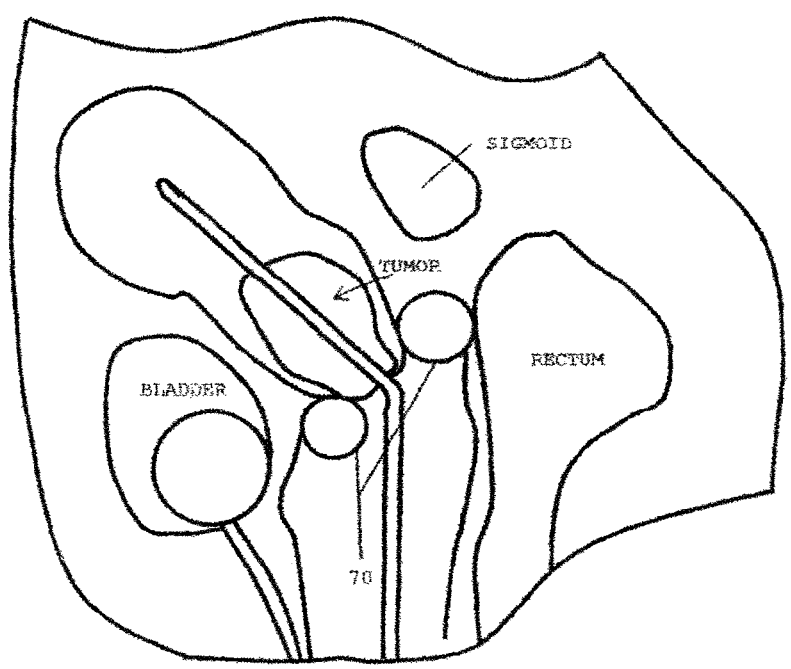
FIG. 16 is a schematic anatomical diagram indicating the most irradiated tissue volumes adjacent to the applicator ring for the rectum, sigmoid and bladder. Shielding added to indicated areas of the ring applicator in conjunction with a flexible source holder.

Gynecological Brachytherapy: In one embodiment, FIG. 16, which is particularly useful in gynecological cervix brachytherapy, the ring applicator 70, mentioned above, can include shielding at strategic locations on its periphery in order to significantly reduce the dose to the non-target bladder and rectum while delivering the desired dose to the cervix. This has the result of reducing the side effects to normal (noncancerous) tissue. Alternatively, this would allow an increase in the dose to the target (cancerous) tissues without increasing the dose to the non-cancerous normal tissues (bladder and rectum) and therefore increase the potential cure rate without increasing the side effects.

Figure 17:
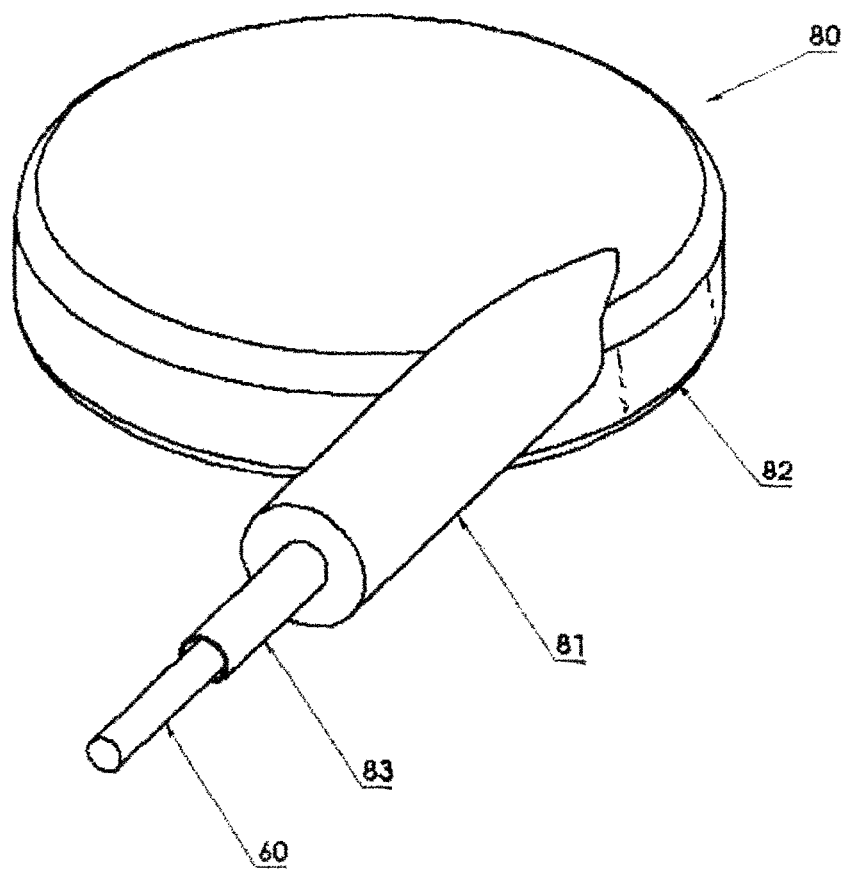
FIG. 17 illustrates a circular applicator including shielding around the periphery in order to significantly reduce the dose to the non-target areas of the eye and surrounding tissue while delivering the desired dose to the tumor.
Figure 18:
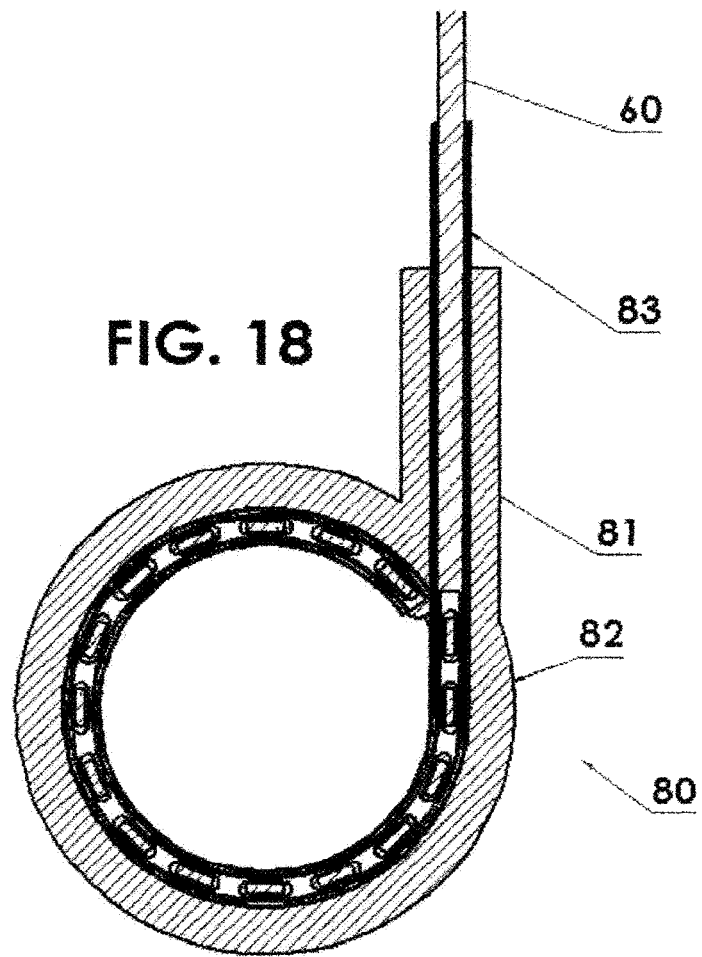
FIG. 18 is a horizontal cross sectional view of FIG. 17.
Figure 19:
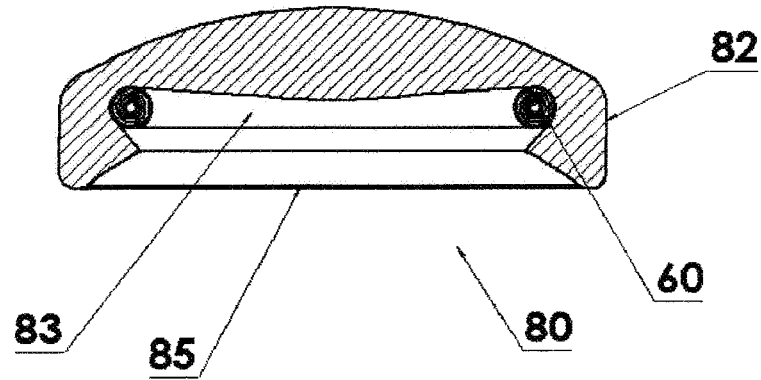
FIG. 19 is a vertical cross sectional view of FIG. 17.
Figure 20:
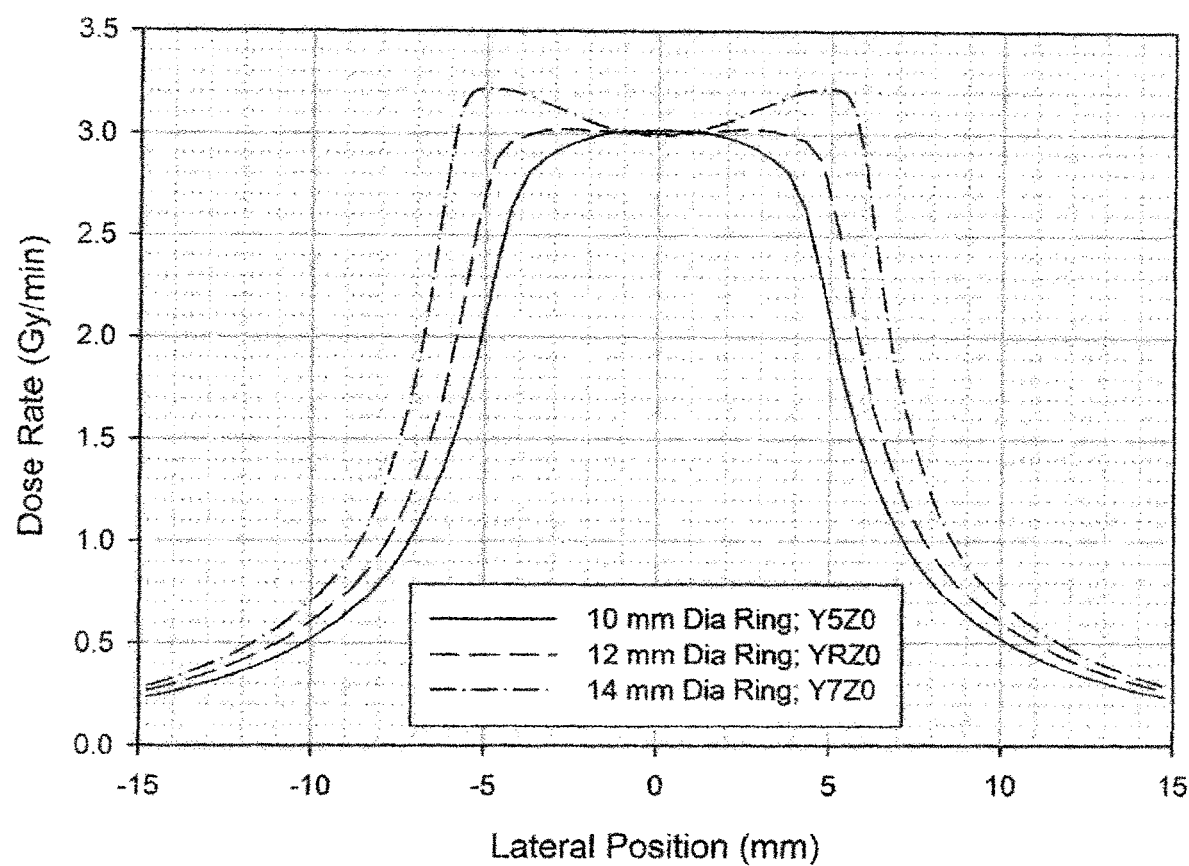
FIG. 20 is a graph of the lateral dose distribution at 5 mm depth from a 12 mm diameter applicator with various conical openings.
Figure 21:
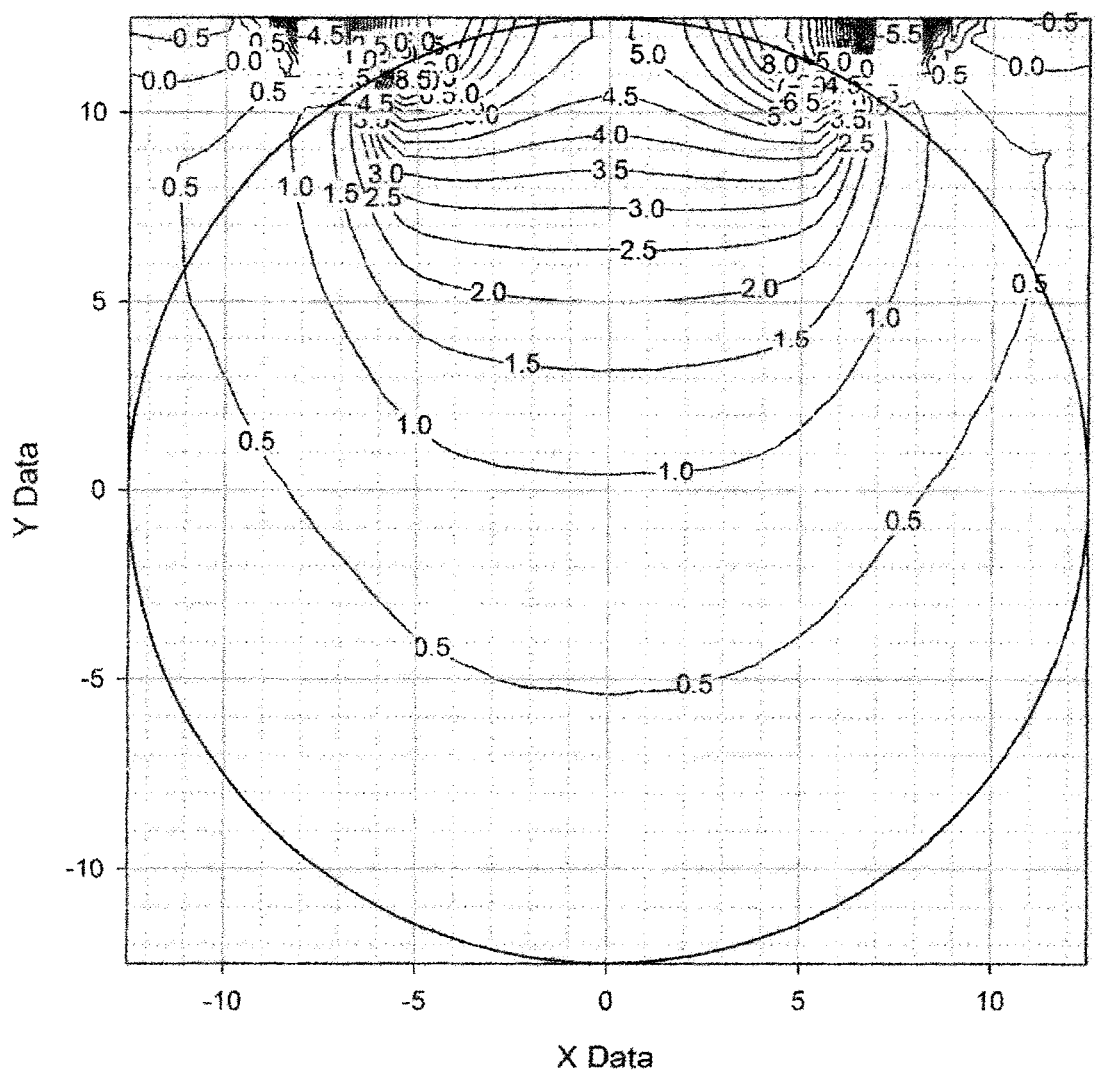
FIG. 21 is an isodose distribution in the X-Z plane from 12 mm diameter applicator with the cone apex at Z=4 mm.
Figure 22:
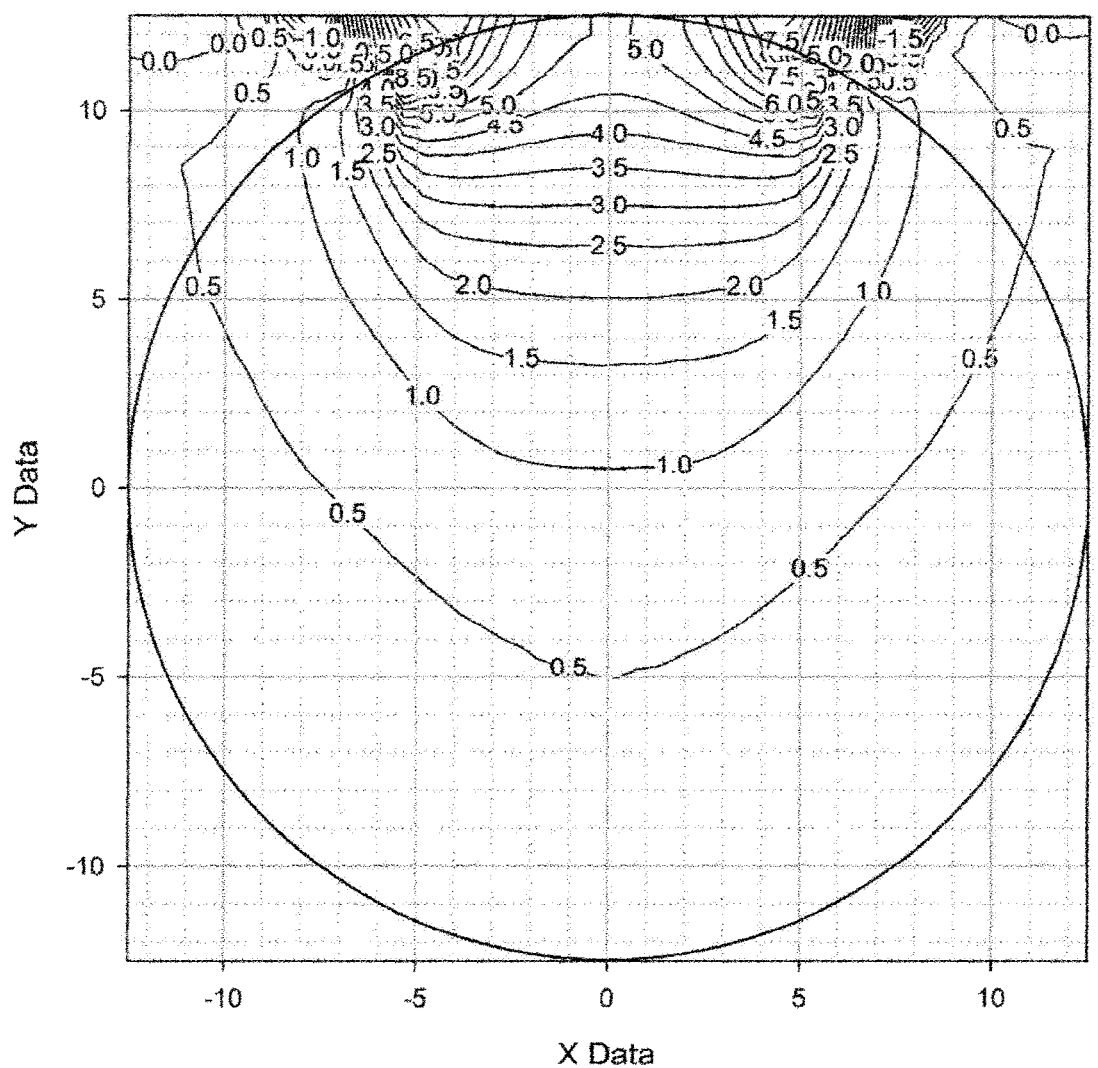
FIG. 22 is like FIG. 21 except the cone apex is at Z=0 mm.
Figure 23:
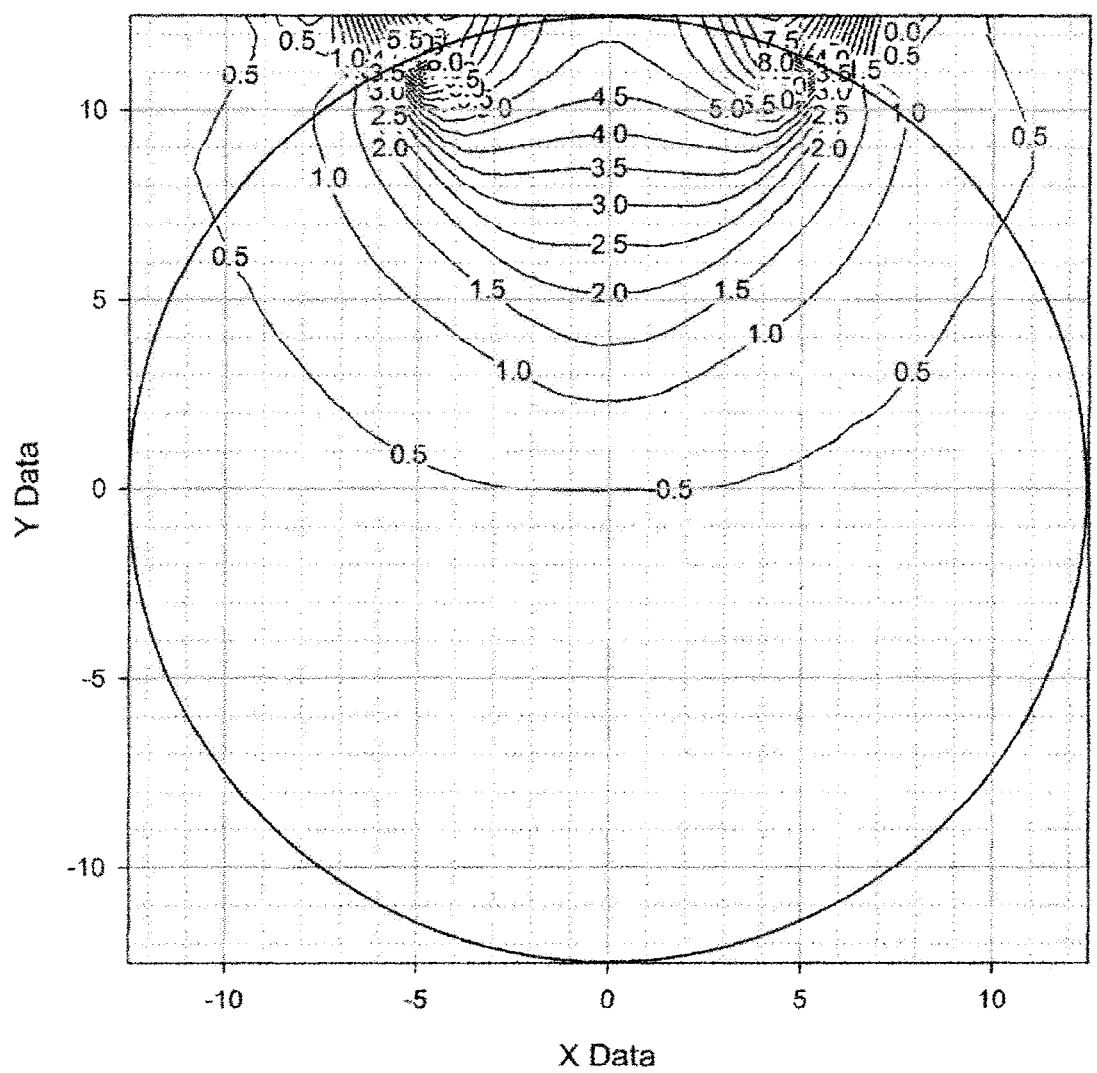
FIG. 23 is like FIG. 21 except the cone apex is at Z=6 mm.

Eye Brachytherapy: In another embodiment, which is particularly useful in eye brachytherapy, a circular applicator 80, FIGS. 17, 18 and 19, can include shielding 82 around the periphery in order to significantly reduce the dose to the non-target areas of the eye and surrounding tissue while delivering the desired dose to the tumor. The circulator applicator 80 includes an input housing 81 having a channel 83 therein into which the source assembly 60 is inserted during treatment. FIG. 18 shows a horizontal cross section through the circulator applicator 80 of FIG. 17. The circulator applicator 80 is shaped like a lid of a bottle as seen in FIG. 19 with the channel 83 thereabout. The interior open volume 85 would be placed over the eyeball during treatment.

FIGS. 20, 21, 22, and 23 show the dose distribution using sources of equivalent activity, which results in axially symmetric dose distributions. However, this invention is equally applicable to sources in which the activity is not equivalent, which results in non-axially-symmetric dose distributions which can be designed to conform to the size and shape of the specific tumor/target. Although these examples show results for applicators in circular configurations, the invention is equally applicable to other curved configurations such as elliptical or other planar or three dimensional curves.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A therapeutic device using radioactive for treatment, said therapeutic device comprising:
    a source assembly for use in brachytherapy, said source assembly comprising:
        a flexible housing, said flexible housing having a nose thereon, said flexible housing being able to negotiate small radii of curvature from about 5 mm to 12 mm around human tissue, organs, and body channels, said flexible housing being a helically wound wire;
        one or more source capsules, said one or more source capsules being removably mounted in said flexible housing, said flexible housing being capable of holding radioactive material therein.

2. The therapeutic device as defined in claim 1, wherein said flexible housing is formed from flexible material, wherein said flexible material is formed into said flexible housing being capable of holding one or more radioactive capsules, said flexible housing comprising different cross sectional shapes.

3. The therapeutic device as defined in claim 1, further including said flexible housing being capable of holding one or more source capsules having dimensions of about 0.5 to 1.5 mm in diameter and a length of from about 2 mm to 10 mm.

4. The therapeutic device as defined in claim 1, wherein said flexible housing is made of metal.

5. The therapeutic device as defined in claim 1, wherein said radioactive material is selected from the group comprising: $^{60}$Cobalt, $^{75}$Selenum, $^{103}$Palladium, $^{125}$Iodine, $^{131}$Cesium, $^{137}$Cesium, $^{145}$Samarium, $^{153}$Gadolinium, $^{170}$Thulium, $^{169}$Ytterbium, $^{181}$Tungsten, $^{192}$Iridium, and $^{198}$Gold or from enriched precursors.

6. The radioactive therapeutic device as defined in claim 5, wherein said radioactive material is $^{192}$Iridium.

7. The therapeutic device as defined in claim 5, wherein said radioactive material is produced from a precursor which has an enrichment of about 80% or greater.

8. The therapeutic device as defined in 1, wherein said flexible housing is capable of holding two or more source capsules, said source capsules being not connected, said flexible housing being capable of bending to radii from about 5 mm to 12 mm.

9. The therapeutic device as defined in claim 2, wherein said flexible housing is made by a process selected from the group: wrapping a strip of material about a spindle, 3D printing, laser cutting, and molding.

10. The therapeutic device as defined in claim 1, wherein said flexible housing is attached to a drive cable.

11. The therapeutic device as defined in claim 1, further including radioactive material in said source capsules.

12. The therapeutic device as defined in claim 2, wherein said cross sectional shapes are selected from the group consisting of the following: round, rectangular, oval, and elliptical.

* * * * *